United States Patent [19]

Johnson

[11] Patent Number: 5,538,399
[45] Date of Patent: Jul. 23, 1996

[54] RESERVOIR ENCLOSURE METHODS

[75] Inventor: Jay G. Johnson, Maple Plain, Minn.

[73] Assignee: SIMS Deltec, Inc., St. Paul, Minn.

[21] Appl. No.: 460,115

[22] Filed: Jun. 2, 1995

Related U.S. Application Data

[62] Division of Ser. No. 145,371, Oct. 28, 1993.

[51] Int. Cl.$^6$ .............................. F04B 23/02; A61M 1/00
[52] U.S. Cl. ............................................................ 417/53
[58] Field of Search ........................... 417/53, 234, 360; 604/153; 128/DIG. 12; 137/343

[56] References Cited

U.S. PATENT DOCUMENTS

| | | |
|---|---|---|
| 3,731,679 | 5/1973 | Wilhelmson et al. . |
| 4,398,908 | 8/1983 | Siposs . |
| 4,416,595 | 11/1983 | Cromie . |
| 4,559,038 | 12/1985 | Berg et al. . |
| 4,565,542 | 1/1986 | Berg . |
| 4,650,469 | 3/1987 | Berg et al. . |
| 4,657,486 | 4/1987 | Stempfle et al. . |
| 5,017,059 | 5/1991 | Davis . |
| 5,078,683 | 1/1992 | Sancoff et al. . |
| 5,165,874 | 11/1992 | Sancoff et al. . |
| 5,181,910 | 1/1993 | Scanlon . |
| 5,324,258 | 6/1994 | Rohrbough . |
| 5,342,313 | 8/1994 | Campbell et al. . |

OTHER PUBLICATIONS

Exhibit Supplemental A: CADD Enclosure brochure (Jan. 1991).
Exhibit Supplemental B: Bard® Ambulatory PCA Infusion Pump Quick Reference Guide (Apr. 1990).
Exhibit Supplemental B–1: Patient Guide for the Bard® Ambulatory PCA Infusion Pump brochure, (undated).
Exhibit Supplemental D: MedMate™ 1100 brochure (undated) (selected pages).
Exhibit Supplemental E: Verifuse® Lock Box Instructions (undated).
Exhibit Supplemental E–1: Verifuse® Ambulatory Infusion System Nurse Guide (©copyright 1991, 1993).
Exhibit Supplemental E–2: Verifuse® Ambulatory Infusion System Patient Guide (©copyright 1991, 1993).
Exhibit Supplemental F: Medfusion Inc., WalkMed™ 420I/C, WalkMed™ 430PCA, WalkMed™ 440PIC brochure (undated).
Exhibit Supplemental F–1: WalkMed™PCA brochure (©1993).
Exhibit G Pharmacia Deltec brochure entitled "CADD® Pump Accessories," dated Apr. 1991.
Exhibit H Pharmacia Deltec brochure entitled "Instructions for Use One Liter Pouch for Pharmacia Deltec Ambulatory Infusion Pumps," dated Apr. 1989.
Exhibit I Pharmacia Deltec brochure entitled "CAD-TPN™ Backpack Diagram", dated Oct. 1990.
Exhibit J Pharmacia Deltec brochure entitled "50–/100–ml Dual Pump Pouch for use with Pharmacia Deltec Ambulatory Infusion Pumps and Accessories Instructions for Use", dated Sep. 1992.

(List continued on next page.)

*Primary Examiner*—Richard A. Bertsch
*Assistant Examiner*—William Wicker
*Attorney, Agent, or Firm*—Merchant, Gould Smith, Edell, Welter & Schmidt

[57] ABSTRACT

A method is provided for protecting a bag containing fluid used in connection with a pump for pumping the fluid to the patient. The pump closes off the opening into an enclosure. A first end of the pump is positioned within the enclosure adjacent to a retaining lip. A latch structure latches a second end of the pump to the enclosure to mount the pump to the enclosure. A bag spike chamber is provided for receiving a bag spike used to connect the pump to the bag. A platform is provided for supporting the bag above the bag spike chamber. A ridge on the front of the control module of the pump engages the enclosure during mounting of the pump to the enclosure. A ridge on the back of the control module fits into the enclosure. The enclosure further includes a pressure plate support surface for engaging a reciprocally shaped pressure plate to facilitate a mechanical fit of the pressure plate to the enclosure.

7 Claims, 6 Drawing Sheets

OTHER PUBLICATIONS

Photographs of a pump product by Patient Solutions, Inc. Med-Mate™, Model 1100, pp. D1–D2, Exhibit D.

Photographs of a pump product by Block Medical, Inc. a Hillenbrand Industry, Verifuse®, Model No. B001500, pp. E1–E5, Exhibit E.

Photographs of a pump product by Medfusion, Inc., a Medex, Inc. Company, Infu–Med™, WalkMed™ 440 PIC, pp. F1–F4, Exhibit F.

Photographs of a look box product by Pharmacia Deltec, pp. A1–A4, Exhibit A.

Photographs of a first pump product by C. R. Bard, Inc. pp. B1–B5 Exhibit B.

Photographs of a second pump product by C. R. Bard, Inc. pp. C1–C5, Exhibit C.

RESERVOIR ENCLOSURE METHODS

This is a Division of U.S. patent application Ser. No. 08/145,371, filed Oct. 28, 1993, which application is incorporated herein by reference.

FIELD OF THE INVENTION

The present invention relates to infusion systems and methods utilizing enclosures for fluid reservoirs including flexible bags.

BACKGROUND OF THE INVENTION

Infusion systems are known which include a fluid reservoir, a pump for pumping fluid from the fluid reservoir to the patient, and a conduit from the fluid reservoir to the pump and from the pump to the patient for transporting the fluid. Typically, the fluid reservoir is a flexible bag made from a polymeric material.

The flexible bags are capable of being punctured or torn by sharp objects. This can be a problem for patients who desire to use the pumps in an ambulatory manner, for example, at home or work. Also, the fluid contained within the bag could be hazardous to the patient or the caregiver should the fluid come in contact with the skin or the eyes. Chemotherapy fluids, for example, can be harmful to the skin and the eyes if the fluid comes in direct contact. Also, the drugs contained within the bags may be controlled substances, such as narcotics, which could be withdrawn from the bag by a needle punctured through the side of the bag.

In addition, when the pump is used in an ambulatory manner, the fluid conduit between the bag and pump is subject to damage from contact with foreign objects or to catching on objects if exposed to the objects. Also, it is desirable for the patient to move about easily when operating the pump in an ambulatory manner.

There is a need for enclosure arrangements to protect the bags used with drug pumps. It is desirable that the enclosure arrangements be easy to use, provide the bag with protection from punctures or tears, and be not too bulky or awkward to use. In addition, there is a need to maintain the bag in close proximity to the pump. There is also a need to protect the fluid conduit between the pump and the bag from stresses applied to the conduit such as caused by pulling on the conduit or pulling on the pump. The present invention addresses at least some of these needs and other needs.

SUMMARY OF THE INVENTION

One aspect of the present invention relates to an enclosure arrangement having a wall construction defining a chamber for receiving a bag of fluid. The enclosure includes an edge which defines an opening for accessing the chamber. The edge is sized to receive the pump when the pump closes off the opening to the chamber to limit access to the bag. The enclosure includes a retaining lip which retains a first end of the pump. A latch arrangement retains a second end of the pump disposed away from the first end to mount the pump to the enclosure. The retaining lip is spaced apart from a back surface of the enclosure such that a portion of the pump, and preferably a portion of the bag are positioned between the retaining lip and the back surface of the enclosure.

In one preferred embodiment, a bag spike chamber is provided for receiving a bag spike used to interconnect the pump to the bag. In another embodiment, the bag includes a tube mounted to the bag in a permanent manner wherein the tube and the bag are discarded as a single unit after use, and the tube includes a portion sized to be utilized by the pump mechanism to pump fluid through the tube to the patient.

The present invention also relates to a pump system including an enclosure defining a chamber. The enclosure includes an edge defining an opening into the chamber, and a retaining lip adjacent the edge. A latch arrangement disposed away from the retaining lip selectively retains a portion of the pump. The pump is partially positioned in the chamber, with a first portion of the pump positioned to engage the retaining lip, and a second portion of the pump disposed away from the first portion engaged by the latch arrangement. A bag containing fluid is located within the chamber. The bag includes a conduit structure for linking the bag to the pump.

The pump preferably includes a ridge structure on the back surface of the pump for receipt within the edge defining the opening to the enclosure. Preferably, the bottom the pump defines a ridge structure for reciprocal engagement by a support surface of the enclosure defined within the chamber. The pump preferably includes a ridge structure on the front surface of the pump for engagement with a portion of the edge defining the opening to the enclosure.

The present invention also relates to a pressure plate for use with a pump including: a body construction having a top surface configured for receipt of a tube, the top surface including two longitudinal edges, and two side edges extending between the two longitudinal edges. The tube extends in a direction generally parallel to the two longitudinal edges. The body construction further has a bottom surface facing in an opposite direction to the top surface, the bottom surface including a three sided ridge configuration having a U-shape, the ridge including a longitudinal surface extending in a direction generally parallel to the two longitudinal edges, and two end surfaces extending from opposite ends of the longitudinal surface transverse to the longitudinal surface. Structure is provided for mounting the tube to the pressure plate.

The present invention also relates to a bag enclosure for use with a fluid pump and a fluid bag, the enclosure including a wall construction including an enclosed chamber and an edge defining an opening into the enclosed chamber, the opening and the enclosed chamber sized to receive the fluid bag and a portion of the fluid pump, the wall construction including a retaining lip wherein a front of the fluid pump is positioned adjacent to the retaining lip, with the fluid bag positioned between a portion of the wall construction opposite the retaining lip and a back of the fluid pump facing in an opposite direction to the front, the edge sized to be closed off by the fluid pump.

The present invention also relates to a method of using an enclosure arrangement wherein a bag of fluid is placed within a chamber of the enclosure arrangement, an end of a pump is placed within the chamber of the enclosure arrangement, and the second end of the pump is latched to the enclosure arrangement. The method preferably includes rotating the second end of the pump toward the opening prior to latching the second end to the enclosure arrangement. At some time prior to closing off the opening by the pump, the pump is interconnected to the bag to provide a fluid passage from the bag to the pump. The pump can then

DETAILED DESCRIPTION OF THE PREFERRED EMBODIMENTS

Figures 1, 2:
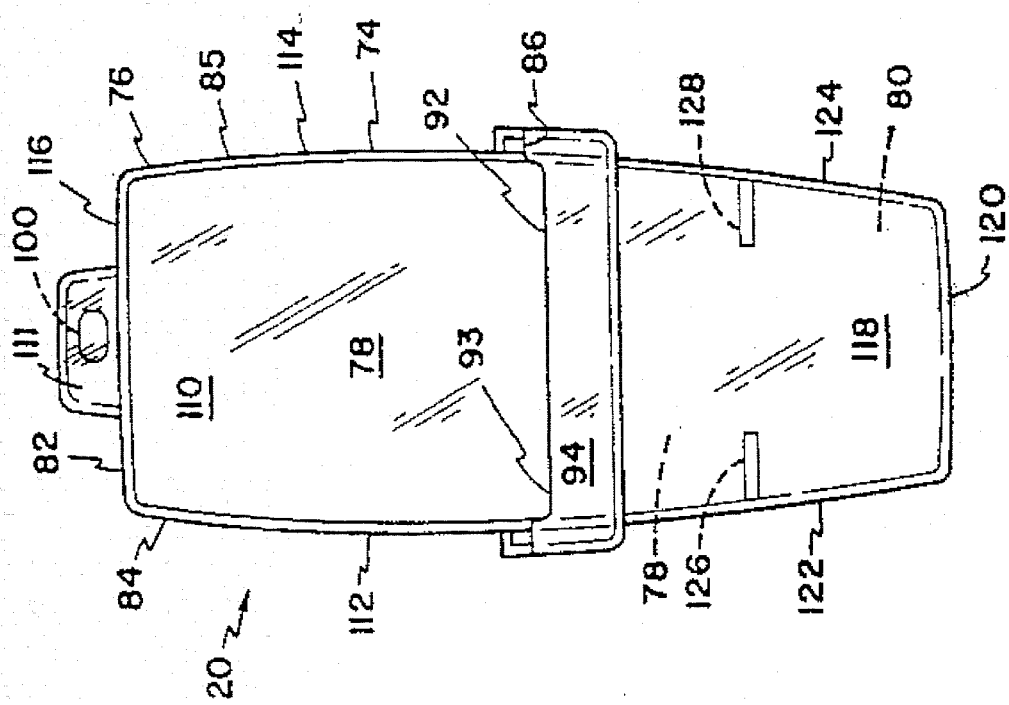
FIG. 1 is a front view of a first embodiment of an enclosure arrangement according to the present invention.
FIG. 2 is a side view of the enclosure arrangement of FIG. 1.

Referring now to FIGS. 1 through 7, a first embodiment of an enclosure arrangement 20 and a pump 22 is shown. Enclosure arrangement 20 (hereinafter referred to as "enclosure") is usable with a fluid containing bag 26 (shown in FIGS. 3 and 4) for protecting the contents of bag 26 during usage with pump 22 (shown in FIGS. 3, 4, and 5B). Enclosure 20 also provides a convenient manner of easily storing and protecting bag 26, pump 22, and the associated fluid conduit arrangement 28 connecting bag 26 to pump 22, and pump 22 to the patient during use.

Enclosure 20 may be used with a standard bag and a bag spike arrangement or other connection structure to selectively connect bag 26 to pump 22. Standard bags are conventional drug or other fluid bags commonly used in the health care industry for a variety of different treatments and therapies. Alternatively, enclosure 20 can be used with custom bags mounted directly to pump 22 without any temporary conduit connection structure.

Figure 3:
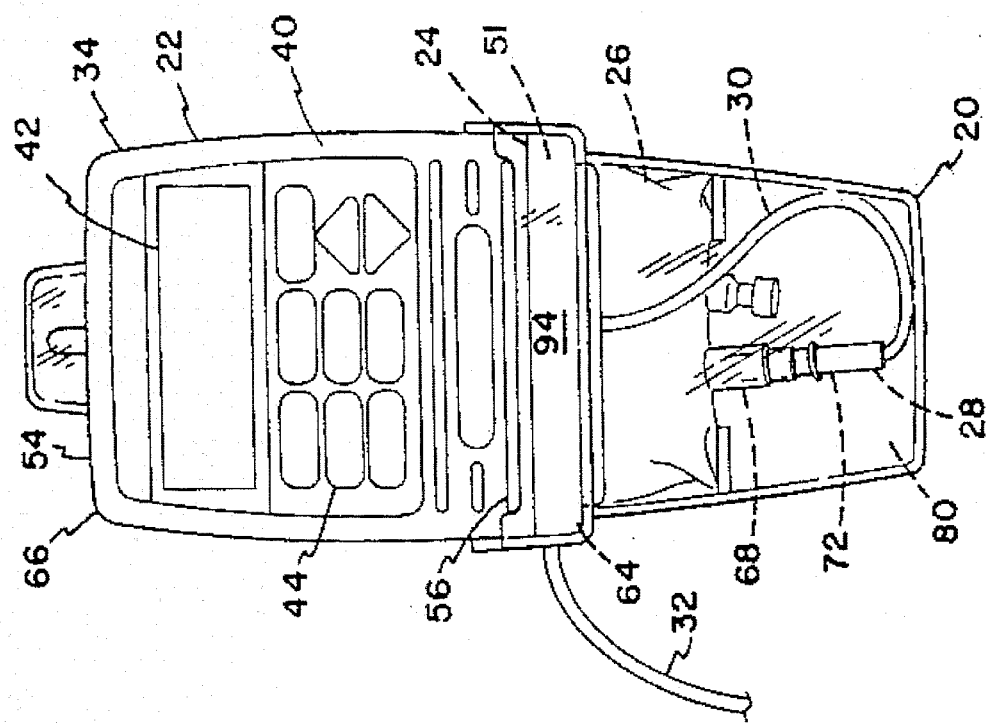
FIG. 3 is a front view of the enclosure arrangement shown in FIGS. 1 and 2 with a pump and a fluid bag mounted thereto.
Figure 4:
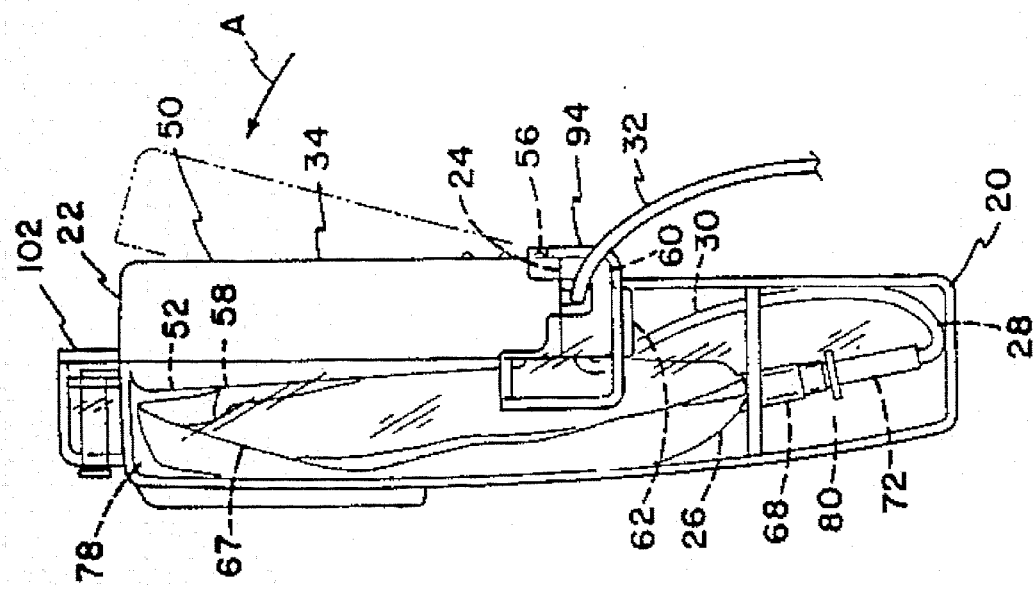
FIG. 4 is a side view of the enclosure arrangement, the pump, and the bag shown in FIG. 3.
Figure 5B:
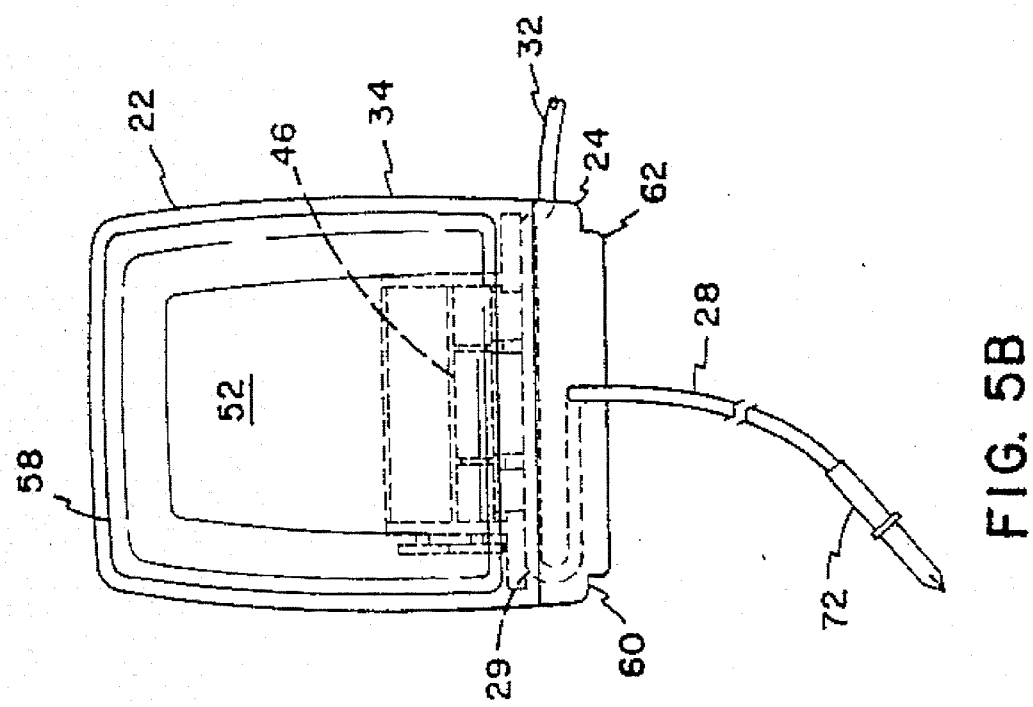
FIG. 5B is a back view of the pump shown in FIGS. 3 and 4.

As shown in FIGS. 3, 4 and 5B, pump 22 includes a pressure plate 24 which is selectively mounted to control module 34. Pressure plate 24 has a generally planar top surface for use in the pumping operation as will be described later. Control module 34 includes an outer housing 40, a display 42, and a keyboard 44. A pump mechanism 46 engages a portion of the fluid conduit arrangement 28 passing between control module 34 and the top planar surface of pressure plate 24. An example of a pump mechanism 46 is disclosed in U.S. Pat. No. 4,559,038, issued Dec. 17, 1985, to Berg et al., the disclosure of which is herein incorporated by reference. The pump mechanism disclosed in U.S. Pat. No. 4,559,038 and shown generally in FIG. 5B herein includes a rotatable cam shaft, and three reciprocally mounted followers (inlet valve, expulser, and outlet valve) which engage a tube in a predetermined manner to pump fluid through the tube. The cam shaft is rotated to cause fluid to be pumped to the patient. Other pump mechanisms are anticipated instead, such as a wave style mechanism, or a rotary or roller style mechanism.

U.S. Pat. No. 4,559,038 also discloses one example of selective mounting structure for mounting pressure plate 24 to control module 34, including two hooked portions, two hinge pins, and an inverted u-shaped member, where the hooked portions extend from the pressure plate and cooperate with the two hinge pins on the control module, and the u-shaped member is engaged by latch/lock structure on the control module.

Referring again to FIGS. 3 and 4, bag 26 is shown interconnected to pump 22 via fluid conduit arrangement 28. A first tube portion 30 connects bag 26 to pressure plate 24. A second tube portion 32 extends from pressure plate 24 to the patient. A third tube portion 29 is engaged by pump mechanism 46 to cause pumping of the fluid. Third tube portion 29 is sized to pump the appropriate amount of fluid per activation of pump mechanism 46.

Pump 22 includes a front surface 50 and a back surface 52 as shown in FIGS. 3, 4, and 5B. Front surface 50 includes a generally linear front ridge 56 protruding therefrom which cooperates with enclosure 20 to mount pump 22 to enclosure 20, as will be discussed below. Front ridge 56 may have other shapes other than linear.

Back surface 52 includes a ridge 58 for cooperating with enclosure 20 to mount pump 22 to enclosure 20, as shown in FIGS. 4 and 5B, as will be discussed below. Ridge 58 need not be generally rectangular (with slightly convexly curved sides) in outer perimeter as shown in FIG. 5B. However, ridge 58 needs sufficient structure to cooperate with enclosure 20 to permit secure mounting of pump 22 to enclosure 20 and to limit access to bag 26.

Figure 7:
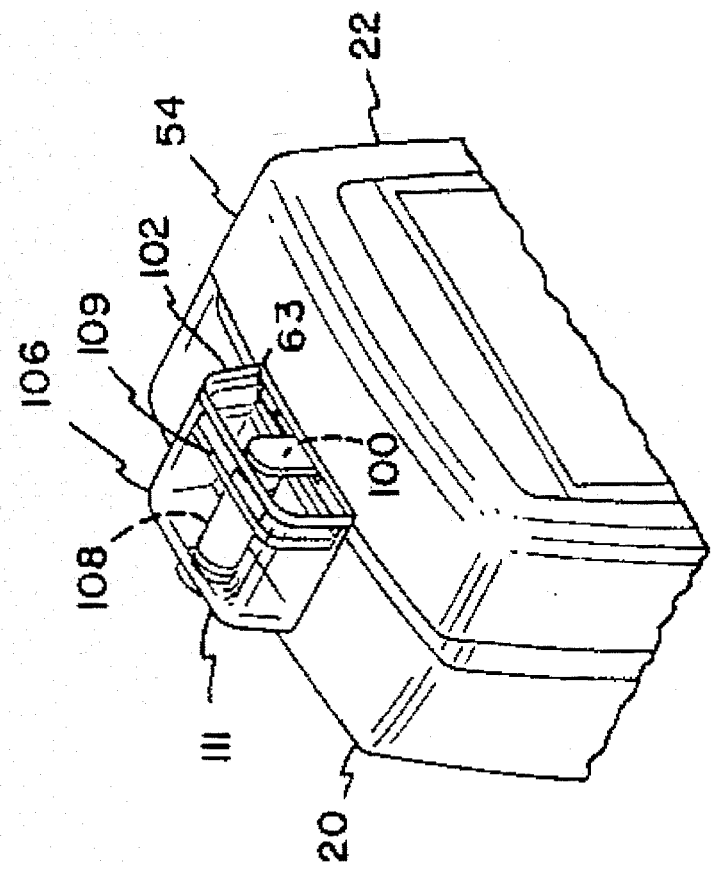
FIG. 7 is a perspective view of the lock arrangement to mount the pump to the enclosure arrangement.

As shown in FIG. 7, a top surface 54 of pump 22 includes a slot 63 for cooperating with latch structure on enclosure 20 to mount pump 22 to enclosure 20, as will be discussed below.

Figure 6:
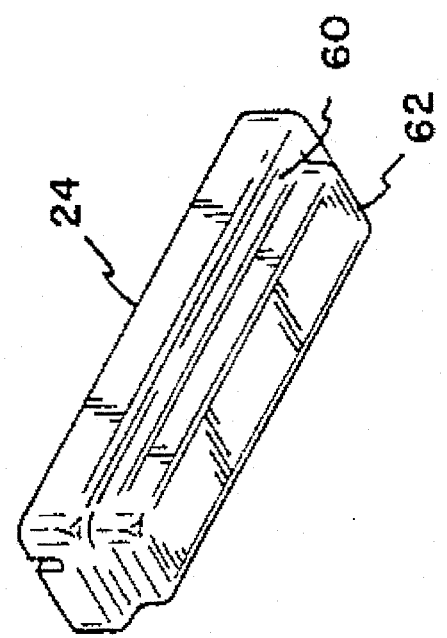
FIG. 6 is a perspective view of the pressure plate of the pump shown in FIGS. 3, 4, and 5B.
Figure 8:
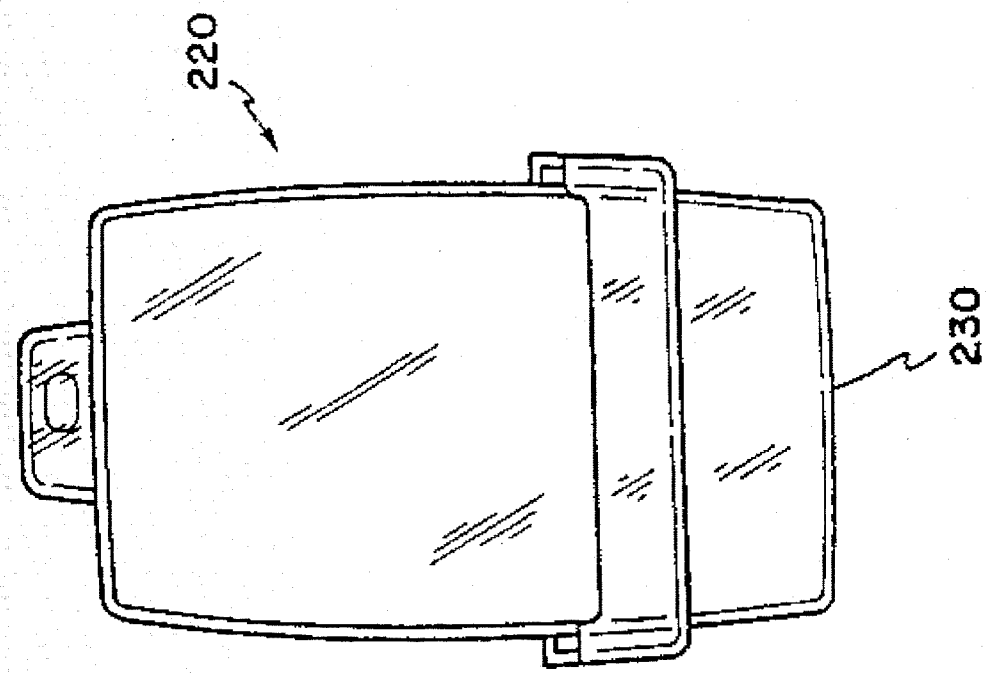
FIG. 8 is a front view of a second embodiment of an enclosure arrangement according to the present invention.
Figure 9:
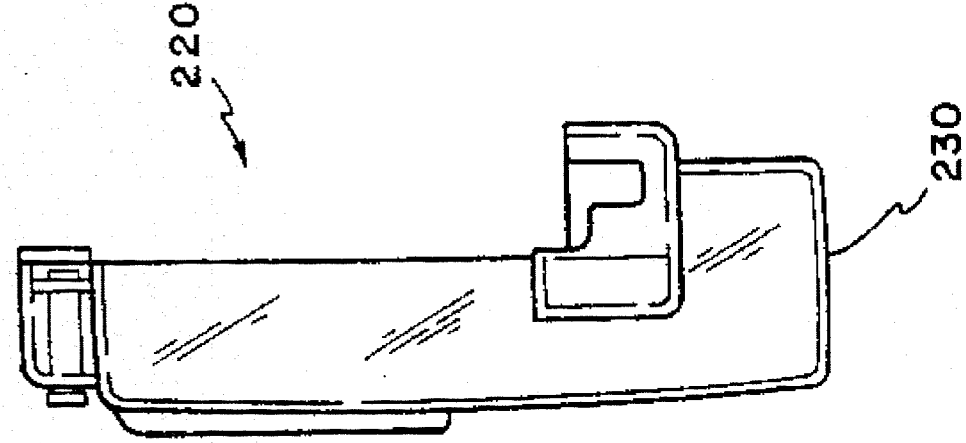
FIG. 9 is a side view of the enclosure arrangement of FIG. 8.

As shown in FIGS. 4 and 6, pressure plate 24 of pump 22 includes a bottom Surface 60 defining a u-shaped ridge 62 (shown with a front longitudinal surface and two side surfaces extending transverse to the front longitudinal surface) for cooperating with reciprocally shaped structure on enclosure 20 during mounting of pump 22 to enclosure 20. Ridge 62 need not be u-shaped in the outer perimeter. However, ridge 62 needs sufficient structure to cooperate with enclosure 20 to permit secure mounting of pump 22 and to limit access to bag 26. Pressure plate 24 includes an appropriately configured top surface positioned adjacent to control module 34 to mount tube portion 29 thereto to properly position tube 29 adjacent to the tube engaging members of pump mechanism 46.

Bag 26 includes a flexible polymeric panel arrangement 67 defining the sides of bag 26 for enclosing a fluid. Outlet 68 permits the insertion of a bag spike 72 which is part of fluid conduit arrangement 28. Bag spike 72 punctures a thin seal (not shown) disposed within outlet 68 to permit fluid contained within bag 26 to exit via outlet 68 and to pass through fluid conduit arrangement 28 for pumping to the patient. Other fluid conduit connectors are anticipated, such as threaded connectors.

Referring now to FIGS. 1 and 2, enclosure 20 includes a wall construction 74 defining structure for receiving bag 26 and structure for receiving pump 22. Edge 76 of wall construction 74 defines an opening into an interior of enclosure 20. Enclosure 20 defines a chamber 78 for receiving bag 26. Chamber 78 is defined by a back panel 110, two side panels 112, 114 interconnected to back panel 110, and a top panel 116 of enclosure 20 interconnected to back panel 110 and both side panels 112, 114. During use, bag 26 is positioned between back panel 110, side panels 112, 114, and top panel 116 of enclosure 20, and back surface 52 of pump 22 within chamber 78 as shown in FIGS. 3 and 4.

In chamber 78, bag 26 is protected from tears or punctures. Similarly, fluid conduit arrangement 28 is protected. In addition, enclosure 20 provides convenient structure for maintaining bag 26 in close proximity to pump 22 in a manner that is easy for the patient to handle and transport.

As shown in FIGS. 3 and 4, enclosure 20 further defines a chamber 80 for bag spike 72 and outlet 68 of bag 26. Chamber 80 is defined by a lower portion of back panel 110, a front panel 118, an end panel 120, and two side panels 122, 124 of enclosure 20. Side panels 122, 124 connect front panel 118 to back panel 110. End panel 120 is interconnected to all of side panels 122, 124, back panel 110, and front panel 118.

Chamber 80 provides a separate compartment for the bag spike 72 and outlet 68. This helps keep first tube portion 30 from being pinched off by pressure from bag 26 or from being kinked in use. Enclosure 20 includes inwardly extending platforms 126, 128 extending from side panels 122, 124 to support bag 26 when enclosure 20 is held vertically with chamber 78 above bag spike chamber 80. Platforms 126, 128 keep bag 26 from falling downward into bag spike chamber 80.

Edge 76 of enclosure 20 includes a top edge portion 82 and two side edge portions 84, 85 extending from top edge portion 82. Ridge 58 on the back surface 52 of pump 22 fits within the periphery defined by top edge portion 82 and side edge portions 84, 85 of edge 76 as shown in FIG. 4. Edge 76 includes a bottom edge portion 86 comprising two opposed sides 88, 89 and a front portion 92 interconnecting sides 88, 89. Side 88 defines a slot 90 for receipt of second tube portion 32 from pump 22 extending to the patient.

Enclosure 20 includes a retaining lip 94 bounded by front portion 92 of edge 76. As shown in FIGS. 3 and 4, a portion of pump 22 fits within the interior of enclosure 20 adjacent retaining lip 94. Portion 51 of front surface 50 of pump 22 is shown in FIGS. 3 and 4 as being positioned inside retaining lip 94 of enclosure 20. In FIG. 4 in the orientation shown, downward movement of pump 22 relative to enclosure 20 is prevented by ridge 56. In FIG. 4, horizontal movement of pump 22 to the left relative to enclosure 20 is prevented by engagement of back surface 52 around an outside of ridge 58 with top portion 82 and side portions 84, 85 of edge 76. Upward movement of pump 22 and lateral movement of pump 22 relative to enclosure 20 is prevented by engagement of ridge 58 with top edge portion 82 and side edge portions 84, 85 of edge 76, respectively.

At an opposite end of pump 22 adjacent top surface 54, enclosure 20 includes a latch arrangement 98 for holding the second end 66 of pump 22 while the first end 64 of pump 22 is held by retaining lip 94. A rotatably mounted detent or projection 100 fits into slot or recess 63 in top surface 54 of pump 22 as shown in FIG. 7. A cover plate 102 covers an opening into a chamber 104 defined by housing 106 of enclosure 22 for protecting detent 100 and limiting access to detent 100. A rotatably mounted shaft 108 permits rotation of detent 100 into and out of engagement with slot 63 of pump 22. First plate 109 and second plate 111 are mounted parallel to one another to support shaft 108.

Once it is desired to access chamber 78 to remove bag 26, such as when bag 26 is emptied or is to be changed, shaft 108 of latch arrangement 98 is turned to release second end 66 of pump from enclosure 20. Pump 22 is then separable from enclosure 20.

Other latch arrangements are possible for selectively holding second end 66 of pump 22 to enclosure 20. Any appropriately configured structure for selectively gripping, holding, or trapping structure on pump 20 is useable. For example, a loop (not shown) could extend from pump 22 and latch arrangement 98 could include a hook (not shown) for holding the loop. Alternatively, a hooked shaped recess (not shown) in pump 22 could be engaged by a hook (not shown), extending from latch arrangement 98. It is also to be appreciated that any of the possible latch arrangements, including the one shown in the Figures in the preferred embodiment, could be reversed in configuration. For example, detent 100 could be pivotally mounted to pump 22, and slot 63 could be positioned in wall construction 74.

Once pump 22 is positioned to close the opening defined by edge 76 of enclosure 20, bag 26 contained within chamber 78 is protected. Needle access to bag 26 is prevented due to ridge 58 and retaining lip 94. Also, fluid conduit arrangement 28 is protected.

Enclosure 20 is preferably made from a polymeric material, preferably molded plastic and preferably at least partially transparent to light to permit viewing of the contents in chamber 78 and chamber 80, such as PVC or polycarbonate.

Latch arrangement 98 can include a tamper-resistant lock for limiting rotation of detent 100 to prevent removal of pump 22 from its mounted position of FIGS. 3 and 4 to prevent unauthorized access to chamber 78 and bag 26 contained within. For example, shaft 108 includes an internal hex head 113 which can only be engaged to rotate shaft 108 by an appropriately shaped tool. Shaft is prevented from free rotation by a friction fit or other structure for use in maintaining shaft 108 in the position selected by the caregiver.

Pump 22 includes ridge 56 on front surface 50 of control module 34. Ridge 56 cooperates with front portion 92 of edge 76 of enclosure 20. In particular, ridge 56 bears any forces applied during mounting of pump 22 to enclosure 20 and during use of pump 22. This is useful in preventing forces from being exerted on pressure plate 24. Such forces could move pressure plate 24 toward control module 34. Such movement could disrupt and alter performance of the pumping mechanism 46 during engagement with the flexible tube portion 29. As shown in FIGS. 1 and 3, front portion 92 of edge 76 includes a recessed region 93 which permits ridge 56 to be surrounded on three sides, a longitudinal side, and two opposite ends of ridge 56. Other shapes are anticipated for functioning as a pivot point and force bearing surface.

One method of mounting pump 22 to enclosure 20 is illustrated in dashed lines in FIG. 4. First end 64 of pump 22 is inserted within enclosure 20 such that a lower portion 51 of front surface 50 is disposed adjacent retaining lip 94, and ridge 56 is adjacent to, and in engagement with, front portion 92 of bottom edge 86. The second end 66 of pump 22 is rotated toward top edge 82 as shown by the arrow A in FIG. 4. Once pump 22 is positioned relative to enclosure 20 such that back ridge 58 is disposed within the periphery defined by top edge 82 and side edges 84, 85, latch arrangement 98 is operated to hold second end 66 of pump 22 relative to enclosure 20. Pump 22 is removed from enclosure 20 in the reverse direction to that shown for mounting pump 22 to enclosure 20 in FIG. 4.

It is to be appreciated that rotation of pump 22 is not necessary for mounting pump 22 to enclosure 20 as illustrated in FIG. 4. However, it is important that a portion of pump 22 be positioned within enclosure 20 at one end, and another end of pump 22 be latched or otherwise selectively held from movement away from enclosure 20. In this manner, pump 22 can remain a separate element from enclosure 20, and then assembled together to protect bag 26 and/or fluid conduit arrangement 28 contained within enclosure 20 when such protection is desired. In some cases, it is not necessary for pump 22 to be operated in combination with enclosure 20. In that case, enclosure 20 is not utilized, and only pump 22 need be provided for use with the patient. In this manner, a more versatile enclosure system and method is provided. Enclosure 20 can be a separate element supplied to caregivers or other customers owning a supply of pumps 22, for example. Pumps 22 all do not have to be supplied with an enclosure 20 in a caregiver's inventory. Only enough enclosures 20 need to be provided for use at any given time with those pumps 22 being used in an ambulatory manner where enclosure 20 is desired, or those pumps being used where secure protection of the drugs is desired, for example. Those pumps 22 where the use of enclosure 20 is not desired do not need to be supplied with an enclosure.

Retention of pump 22 with enclosure 20 is described as being at "opposite ends" of pump 22. However, it is to be appreciated that spaced apart portions not comprising "opposite ends" of pump 22 may be held relative to enclosure 20 in other embodiments in accordance with the invention.

Pressure plate 24 of pump 22 includes a ridge 62 which cooperates with a u-shaped support surface 96 of enclosure 20 which is shaped to conform to pressure plate 24. In the embodiment shown in FIGS. 3 and 4, support surface 96 defines a platform to conform to a non-planar surface 60 of pump 22. The cooperation between ridge 62 and support surface 96 permits a mechanical fit of enclosure 20 and pump 22. In this manner, pump 22 utilized with other pressure plates not shaped to conform to support surface 96 will not permit the mounting of pump 22 to enclosure 20 in that configuration of pump 22. Such mechanical non-fit can be utilized in the case of pressure plates not configured for use with enclosure 20 of the type that might incur a pinched tube if pump 22 was utilized with enclosure 20. For example, the preferred embodiment utilizes a pressure plate 24 wherein the first tube portion 30 connects from bag 26 to the pressure plate 24 adjacent a longitudinal side of pressure plate 24 instead of an end of pressure plate 24. Some pressure plates 24 are known which provide a connection from bag 26 to pressure plate 24 at an end of pressure plate 24 opposite from the end exiting from pressure plate 24 as shown in FIGS. 3 and 4 for second tube portion 32 connecting pump 22 to the patient. There is a danger tube portion 30 could become pinched if pump 22 is mounted to enclosure 20 and the tube enters pressure plate 24 at the opposite end, unless enclosure 20 is shaped to accommodate such a configuration. The mechanical non-fit of those known pressure plates is useful to prevent pinching off of the tube 30. Other shapes are anticipated for ridge 62 and support surface 96 that will function to provide a mechanical fit/non-fit in the appropriate manner.

Figure 5A:
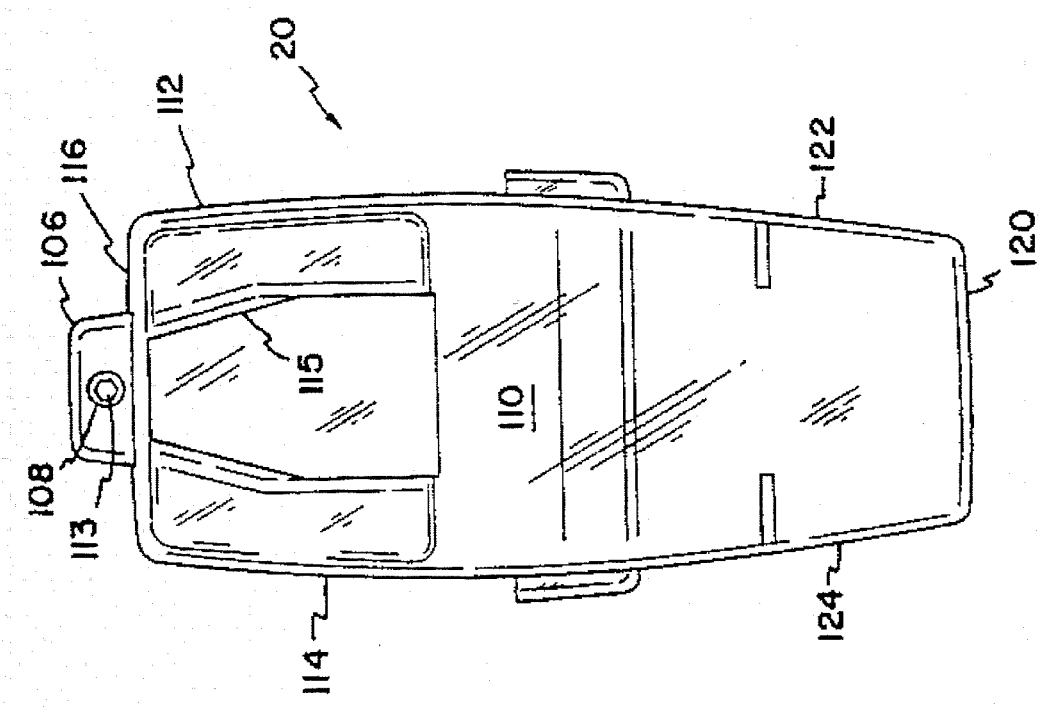
FIG. 5A is a back view of the enclosure arrangement shown in FIGS. 1 and 2.

Referring to FIG. 5A, an exterior of back panel 110 of enclosure 20 includes a mounting arrangement 115 for mounting enclosure 20 to a plate of a pole mounting system. Alternatively, back panel 110 could include other mounting structures for mounting enclosure 20 to another object, such as a pole, a bed head board, or a belt to be worn by the patient.

Referring now to FIGS. 8 through 11, a second embodiment of an enclosure 220 is shown. Enclosure 220 is configured for use with a bag 226 manufactured with pressure plate 224 in a configuration that provides a permanent fluid connection therebetween. No separate bag spike or other temporary bag connection structure and bag are provided. Pressure plate 224 includes a permanent mounting of conduit 228 from bag 226 to pump 222.

In the embodiment of FIGS. 8 through 11, enclosure 220 includes a bottom 230 for engaging bag 226, instead of platforms 126, 128.

Figure 10:
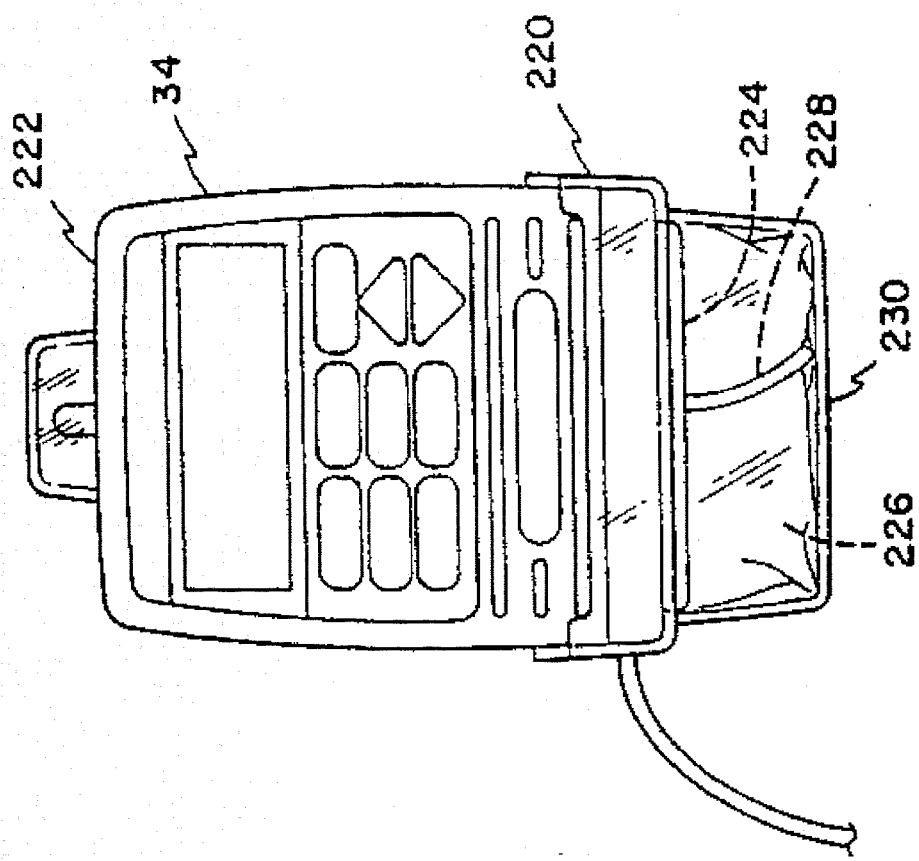
FIG. 10 is a front view of the enclosure arrangement shown in FIGS. 8 and 9 with a pump and a fluid bag mounted thereto, and showing a different pressure plate.
Figure 11:
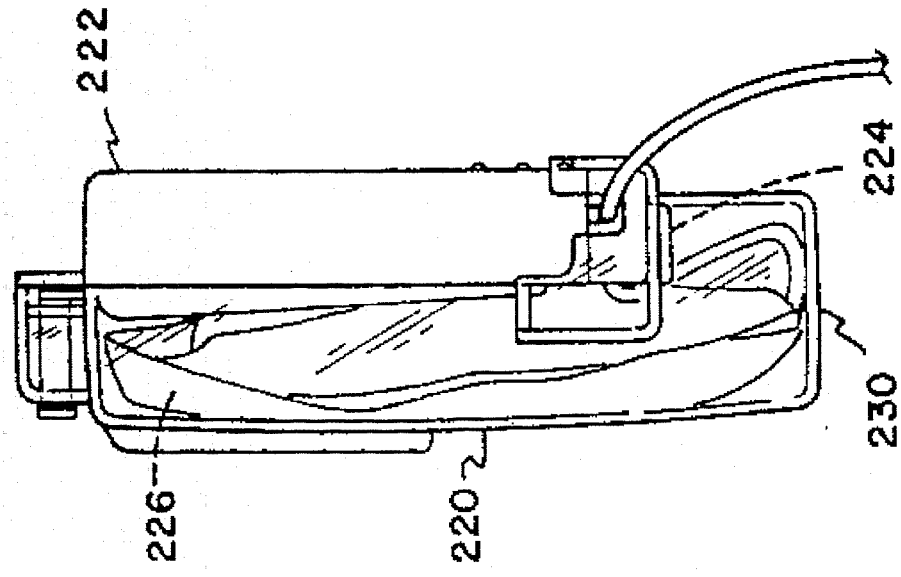
FIG. 11 is a side view of the enclosure arrangement, the pump, and the bag shown in FIG. 10.

Pump 222 shown in FIGS. 10 and 11 is identical to pump 22 shown in FIGS. 3, 4, and 5B with respect to control module 34, except, instead of pressure plate 24, pressure plate 224 is provided. Pressure plate 224 differs only in that there is no bag spike, and conduit arrangement 228 is permanently connected between pressure plate 224 and bag 226 such that when bag 226 is emptied, bag 226 and pressure plate 224 is discarded, along with conduit arrangement 228, as a single unit. The remaining features of enclosure 220 are the same as described for enclosure 20.

While the present invention has been described in connection with the preferred embodiments thereof, it will be understood many modifications will be readily apparent to those skilled in the art, and this application is intended to cover any adaptations or variations thereof. It is manifestly intended this invention be limited only by the claims and equivalents thereof.

What is claimed is:

1. A method of using an enclosure arrangement comprising the steps of:

providing a wall construction defining an internal chamber, the wall construction including an edge defining an opening into the chamber, a retaining lip adjacent to the edge, and a back wall disposed opposite to the retaining lip;

placing a reservoir into the chamber of the wall construction through the opening into the wall construction;

placing a first end of a pump into the chamber of the wall construction through the opening into the wall construction, wherein the first end of the pump is positioned between the retaining lip and the back wall; and attaching a second end of the pump to the wall construction to close off at least a portion of the opening into the wall construction.

2. The method of claim 1, further comprising the step of rotating the second end of the pump toward the opening to close the opening prior to attaching the second end to the wall construction.

3. The method of claim 1, further comprising the steps of:

providing the pump with a back ridge on the back of the pump; and positioning the back ridge within the chamber.

4. The method of claim 1, further comprising the steps of:

providing the pump with a front ridge on the front of the pump;

providing the wall construction with an edge portion having a reciprocal shape to the front ridge; and positioning the front ridge adjacent the edge portion.

5. The method of claim 1, further comprising the steps of:

providing the pump with a bottom ridge on the bottom of the pump;

providing the wall construction with a support surface in the chamber having a reciprocal shape to the bottom ridge; and positioning the bottom ridge within the chamber adjacent the support surface.

6. The method of claim 1, wherein the fluid reservoir is a fluid bag.

7. The method of claim 6, further comprising the steps of:

providing the wall construction with an internal bag spike chamber separate from the chamber for receiving the bag and the pump;

connecting a bag spike to the bag and to the pump; and placing the bag spike into the bag spike chamber of the wall construction through the opening into the wall construction prior to attaching the second end of the pump to the wall construction.

* * * * *